United States Patent
Burns et al.

(10) Patent No.: US 9,446,517 B2
(45) Date of Patent: Sep. 20, 2016

(54) FAULT REACTION, FAULT ISOLATION, AND GRACEFUL DEGRADATION IN A ROBOTIC SYSTEM

(71) Applicant: Intuitive Surgical Operations, Inc., Sunnyvale, CA (US)

(72) Inventors: Christopher R. Burns, San Jose, CA (US); Vaughn Fuelling, Redwood City, CA (US); Gregory K. Toth, Los Altos, CA (US); Akash Patel, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/496,768

(22) Filed: Sep. 25, 2014

(65) Prior Publication Data

US 2015/0112481 A1    Apr. 23, 2015

Related U.S. Application Data

(60) Provisional application No. 61/891,960, filed on Oct. 17, 2013.

(51) Int. Cl.
 *G05B 19/418* (2006.01)
 *B25J 9/16* (2006.01)
 *B25J 9/00* (2006.01)

(52) U.S. Cl.
 CPC ............ *B25J 9/1674* (2013.01); *B25J 9/0084* (2013.01); *G05B 2219/31366* (2013.01); *G05B 2219/40204* (2013.01); *G05B 2219/40205* (2013.01); *Y10S 901/02* (2013.01)

(58) Field of Classification Search
 CPC combination set(s) only.
 See application file for complete search history.

(56) References Cited

U.S. PATENT DOCUMENTS

| | | | |
|---|---|---|---|
| 5,404,290 A | 4/1995 | Tsuchihashi et al. | |
| 5,951,609 A * | 9/1999 | Hanson | B64G 1/24 244/158.8 |
| 7,665,647 B2 * | 2/2010 | Shelton, IV | A61B 17/07207 227/175.1 |
| 7,669,746 B2 * | 3/2010 | Shelton, IV | A61B 17/07207 227/175.1 |

(Continued)

FOREIGN PATENT DOCUMENTS

| | | | |
|---|---|---|---|
| EP | 1813207 A1 * | 8/2007 | ....... A61B 17/07207 |
| EP | 2090241 A1 * | 8/2009 | ....... A61B 17/07207 |

OTHER PUBLICATIONS

International Search Report and Written Opinion for Application No. PCT/US14/59044, mailed on Jan. 21, 2015, 9 pages.

(Continued)

*Primary Examiner* — Bhavesh V Amin

(57) ABSTRACT

A robotic system has arms, arm processors, arm supervisor, and system supervisor. Each arm includes nodes for controlling motors in the arm. Each node, including each arm processor, detects faults affecting the node, places the node into a safe state upon detecting a fault, propagates a fault notification, diagnoses the fault and classifies it, and sends an error message to the supervisor processor. The arm supervisor may detect faults affecting an arm and also perform fault reaction activities. The system supervisor handles the fault as either a system or local fault depending upon its class. For system faults, a fault notification is sent to the arm processors of non-failed arms so that the non-failed arms are placed in the safe state. For local faults, a degraded operation option is provided to a user and if the fault is classified as recoverable, a recovery option is provided to the user.

18 Claims, 7 Drawing Sheets

(56) References Cited

U.S. PATENT DOCUMENTS

| | | | |
|---|---|---|---|
| 7,673,780 B2* | 3/2010 | Shelton, IV | A61B 17/07207 227/175.1 |
| 2002/0167229 A1 | 11/2002 | Agne | |
| 2004/0260481 A1* | 12/2004 | Heiligensetzer | B25J 9/1674 702/33 |
| 2007/0090694 A1* | 4/2007 | Pullmann | H01H 47/002 307/112 |
| 2007/0147250 A1* | 6/2007 | Druke | A61B 19/22 370/235 |
| 2007/0147385 A1* | 6/2007 | Druke | H04L 1/0083 370/394 |
| 2007/0150631 A1* | 6/2007 | Druke | A61B 19/2203 710/244 |
| 2011/0028894 A1* | 2/2011 | Foley | A61B 19/2203 604/95.01 |
| 2012/0039162 A1 | 2/2012 | Druke et al. | |
| 2012/0158012 A1 | 6/2012 | Sandhu et al. | |
| 2012/0316573 A1 | 12/2012 | Durant et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US14/59044, mailed on Apr. 28, 2016, 6 pages.

* cited by examiner

FAULT REACTION, FAULT ISOLATION, AND GRACEFUL DEGRADATION IN A ROBOTIC SYSTEM

CROSS REFERENCE TO RELATED APPLICATIONS

This application claims the benefit of provisional U.S. Patent Application No. 61/891,960 filed Oct. 17, 2013, which is incorporated herein in reference.

FIELD OF INVENTION

The present invention generally relates to robotic systems and in particular, to fault reaction, fault isolation, and graceful degradation in a robotic system.

BACKGROUND

Robotic systems having one or more user controlled robotic arms are used in many applications. As one example, see U.S. Pat. No. 7,865,266 B2, entitled "Cooperative Minimally Invasive Telesurgical System," which is incorporated herein by reference. Additional examples may be found in manufacturing, construction, hazardous material handling, and other applications such as those using teleoperation.

Failures or faults may occur in the robotic arms during their operation that result in loss of full control. To avoid such loss, fault tolerant systems may be employed such as those providing triple redundancy so that a fault may be readily determined and if one component fails, a surviving component may still provide the function. Providing redundant components, however, adds to system cost. Alternatively, preventive maintenance techniques may be employed to minimize the occurrences of such faults. However, unexpected faults may still occur.

When a fault or failure is detected in a robotic system, the entire system may be turned off for safety reasons until the fault can be corrected. Sometimes, however, the robotic system may still be usable to accomplish a primary or secondary task in a degraded state. In this case, it may be advantageous to allow the system to continue operating in the degraded state. Other times, the fault may not be persistent. In this case, clearing the fault and continuing full use of the robotic system may be possible.

OBJECTS AND SUMMARY OF THE INVENTION

Accordingly, one object of one or more aspects of the present invention is a fault handling scheme which ensures that the system is automatically placed in a safe state upon detection of a fault.

Another object of one or more aspects of the present invention is a fault handling scheme which facilitates a graceful degradation of the robotic system after detection of a fault that cannot be cleared.

These and additional objects are accomplished by the various aspects of the present invention, wherein briefly stated, one aspect is a method for fault reaction, fault isolation, and graceful degradation in a robotic system having a plurality of robotic arms. The method comprises: detecting a fault in a failed arm of the plurality of robotic arms; placing the failed arm into a safe state; determining whether the fault should be treated as a system fault or a local fault; and placing non-failed arms of the plurality of robotic arms in the safe state only if the fault is to be treated as a system fault.

Another aspect is a robotic system comprising: a plurality of robotic arms, a plurality of arm processors, and a supervisor processor. Each arm processor is operatively coupled to a corresponding one of the plurality robotic arms. Each robotic arm has a plurality of motors for actuating degrees of freedom movement of the robotic arm. Each robotic arm has one or more nodes for controlling corresponding motors of the robotic arm. Each node and arm processor is configured to detect an occurrence of a fault affecting the node or arm processor, to place the node or arm processor into a safe state upon detecting the occurrence of the fault, to propagate a fault notification through a failed arm that includes the node or is operatively coupled to the arm processor, to diagnose the fault, and to send an error message including information of the fault to the supervisor processor. Each node and arm processor is also configured to place the node or arm processor into a safe state upon receiving a fault notification from another source. The supervisor processor is configured to receive the error message from the failed node or arm processor, to determine whether the detected fault should be treated as a system fault or a local fault by using information in the error message, and to transmit a fault notification to arm processors corresponding to all non-failed arms of the plurality of robotic arms only if the detected fault is to be treated as a system fault.

Additional objects, features and advantages of the various aspects of the present invention will become apparent from the following description, which should be taken in conjunction with the accompanying drawings.

DETAILED DESCRIPTION

Figure 1:
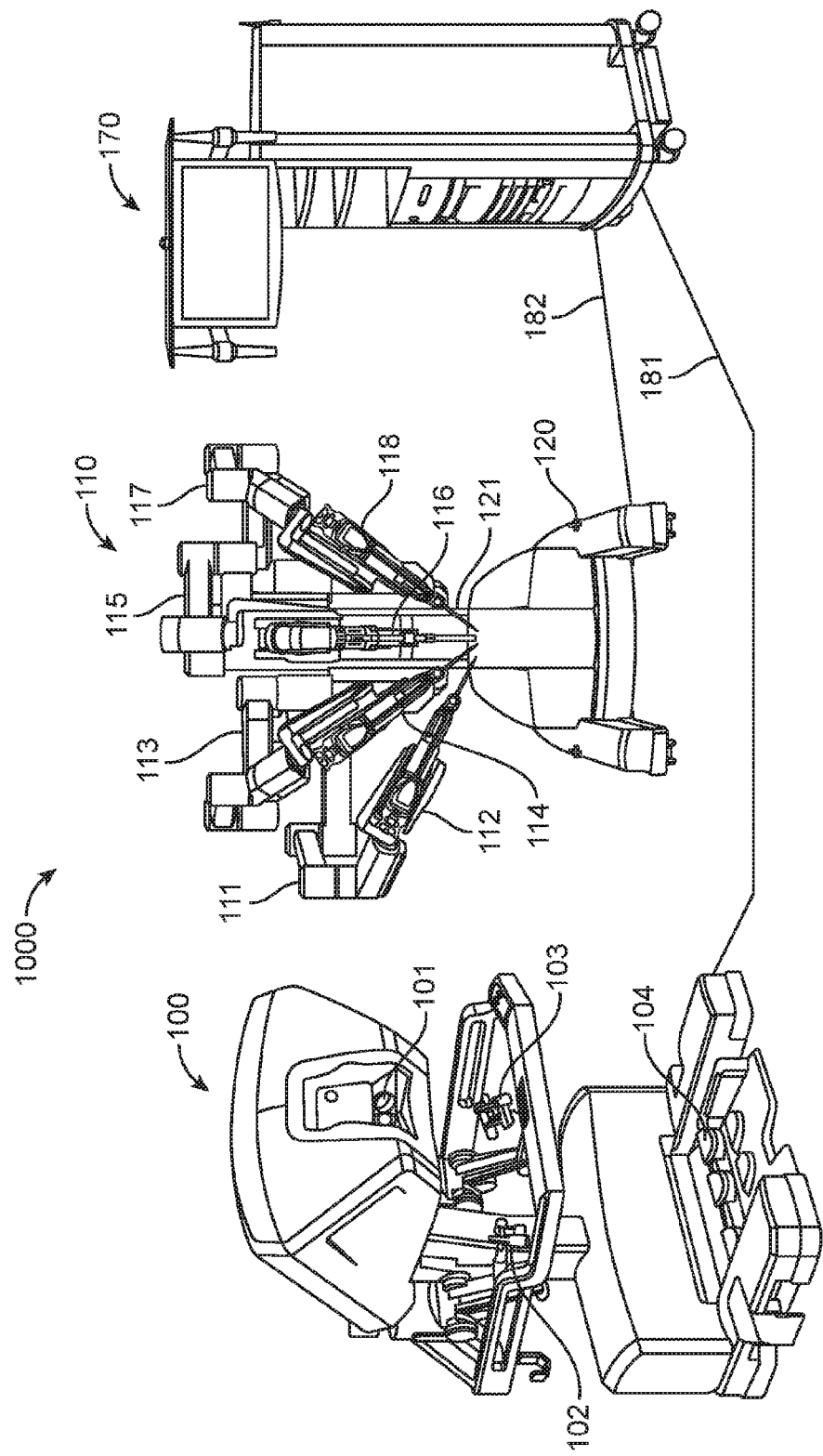
FIG. 1 illustrates a perspective view of a robotic system having a plurality of robotic arms.

FIG. 1 illustrates, as an example, a perspective view of a robotic system 1000 that includes a user console 100, a robotic arms cart 110, and a vision cart 170, which communicate with one another through cables 181, 182. The user console 100 includes a stereo viewer 101, hand-manipulatable master controllers 102, 103, and at least one foot pedal 104. The robotic arms cart 110 includes a base 120, a column 121 that is attached to the base 120, and robotic arms 111, 113, 115, 117 that are attached to the column 121 and that are adapted to hold, move and manipulate attachable instruments 112, 114, 116, 118.

In the example of FIG. 1, the robotic arms 111, 113, 117 hold tool instruments 112, 114, 118 and the robotic arm 115 holds a stereoscopic camera instrument 116. Alternatively, each of the robotic arms 111, 113, 115, 117 may hold a different type of instrument or hold no instrument at all while a work procedure is being performed. As an example, a second image capture device employing a different imaging modality may replace the tool instrument 112 being held by the robotic arm 111. As another example, robotic arm 111 may be left unused with no instrument attached to it during all or a part of a work procedure.

The stereoscopic camera instrument 116 captures stereo images which are continuously transmitted as a video stream to the vision cart 170. The vision cart 170 processes each pair of stereo images as it is received and transmits the processed pair of stereo images to the user console 100 for display on the stereo viewer 101 in real time. Thus, an user may view stereo images of a work site which have been captured by the stereoscopic camera instrument 116 while telerobotically manipulating the tool instruments 112, 114, 118 and/or the stereoscopic camera instrument 116 by manipulating associated ones of the master controllers 102, 103 and/or foot pedal 104. Master/slave control systems are provided in the robotic system 1000 to facilitate such telerobotic manipulations.

The robotic arms 111, 113, 115, 117 may be moved up or down in a vertical direction (e.g., towards the ceiling or towards the floor). Each of the robotic arms 111, 113, 115, 117 preferably includes a manipulator and a set-up arm. The manipulator is adapted to hold an instrument and manipulate it about a pivot point. The set-up arm is adapted to horizontally translate the manipulator in space so that the manipulator's held instrument and the instrument's pivot point are also horizontally translated in space.

Figure 2:
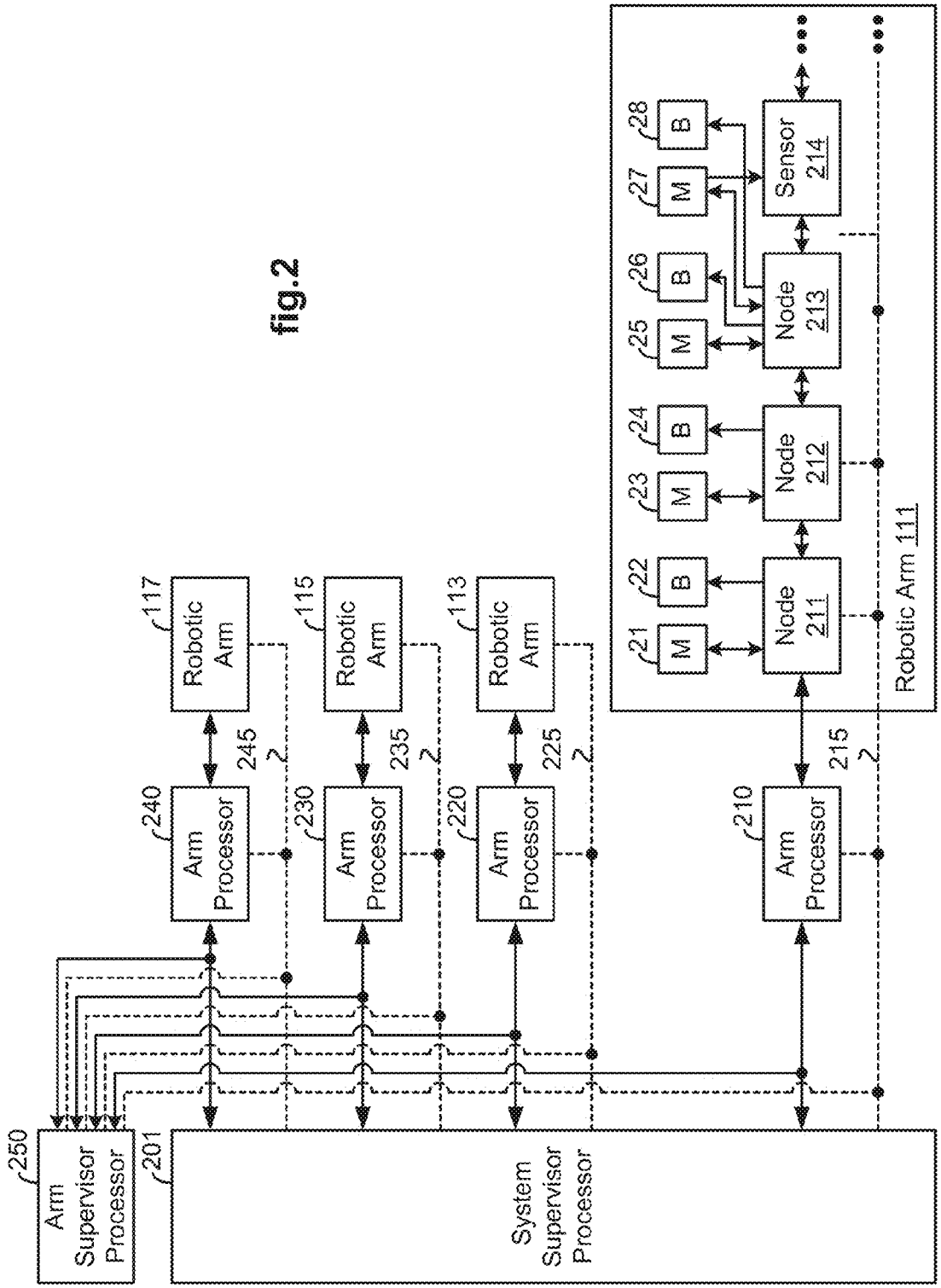
FIG. 2 illustrates a block diagram of components of the robotic system that cooperatively interact to provide aspects of fault reaction, fault isolation, and graceful degradation in the robotic system.

FIG. 2 illustrates, as an example, a block diagram of components of the robotic system 1000 that cooperatively interact to perform various aspects of fault reaction, fault isolation, and graceful degradation in the robotic system 1000. Each of the robotic arms 111, 113, 115, 117 comprises one or more nodes. Each node controls one or more motors which actuate joints and/or linkages in the robotic arm to effect the degrees of freedom movement of the robotic arm. Each node also controls one or more brakes for stopping the rotation of the motors.

As an example, the robotic arm 111 has a plurality of motors (e.g., 21, 23, 25, 27), a plurality of brakes (e.g., 22, 24, 26, 28), and a plurality of nodes (e.g., 211, 212, 213). Each of nodes 211, 212 controls a single motor/brake pair. Node 213, on the other hand, controls two motor/brake pairs. Other nodes (not shown) may control more than two motor/brake pairs. A sensor processing unit 214 is included to provide motor displacement sensor information to the node 213 for control purposes. Although three nodes are shown in the robotic arm 111, it is to be appreciated that more or less nodes may be employed depending upon both the number of motors required to effect the degrees of freedom movement of the robotic arm 111 and the number of motors that are controlled by each node. Robotic arms 113, 115, 117 are similarly configured as robotic arm 111 with motors, brakes, and nodes.

Each robotic arm is operatively coupled to an arm processor. In particular, arm processor 210 is operatively coupled to nodes of the robotic arm 111, arm processor 220 is operatively coupled to nodes of the robotic arm 113, arm processor 230 is operatively coupled to nodes of the robotic arm 115, and arm processor 240 is operatively coupled to nodes of the robotic arm 117. In addition to performing various processing tasks described herein, each arm processor includes a joint position controller for converting desired joint positions $\hat{\theta}_C$ of its operatively coupled robotic arm to current commands $\hat{I}_C$ for driving motors in its operatively coupled robotic arm to actuate their respective joints to the desired joint positions.

A system supervisor processor 201 (also referred to herein as simply "system supervisor") is operatively coupled to the arm processors 210, 220, 230, 240. In addition to performing various processing tasks described herein, the system supervisor processor 201 translates user manipulation of input devices associated with the robotic arms into desired joint positions $\hat{\theta}_C$. Although shown as separate units, the arm processors 210, 220, 230, 240 may also be implemented as part of the system supervisor processor 201 by program code.

An arm supervisor processor 250 (also referred to herein as simply "arm supervisor") is operatively coupled to the system supervisor processor 201 and the arm processors 210, 220, 230, 240. The arm supervisor processor 250 initiates, controls, and/or monitors certain coordinated activities of the arms so as to free the system supervisor processor 201 from having to do so. Although shown as a separate unit, the arm supervisor 250 may also be implemented as part of the system supervisor processor 201 by program code.

Although described as processors and nodes, it is to be appreciated that each of the processors and nodes may be configured to perform the various tasks described herein by any combination of hardware, firmware, and software programming. Also, their functions as described herein may be performed by one unit or divided up among a number of subunits, each of which may be implemented in turn by any combination of hardware, firmware, and software programming. Further, the system supervisor processor 201 may be distributed as subunits throughout the system 1000, such as in the user console 100, vision cart 170, and the base 120 of the robotic arms cart 110. Still further, the system supervisor processor 201, the arm supervisor processor 250, and each of the arm processors 210, 220, 230, 240 may include a plurality of processors to perform the various processor and/or controller tasks and functions described herein.

Each node and sensor processing unit includes a transmitter/receiver (TX/RX) pair to facilitate communications with other nodes of its robotic arm and the arm processor operatively coupled to its robotic arm. The TX/RXs are networked in this example in a daisy chain. In such a daisy chain arrangement, when each node's RX receives a packet of information from an adjacent node's TX, it checks a destination field in the packet to determine if the packet is intended for its node. If the packet is intended for its node, the node processes the packet. On the other hand, if the packet is intended for another node, the node's TX passes the received packet to an adjacent node's RX in an opposite direction from whence it came. Information is preferably communicated over the daisy chain network in packets using a packet-switching protocol. For additional details on such a packet-switching protocol, see, e.g., U.S. Pat. No. 8,054,752 entitled "Synchronous Data Communication," which is incorporated herein by reference.

A fault reaction logic (FRL) line is provided in each robotic arm so that fault notifications may be quickly propagated through the arm. As an example, robotic arm 111 includes an FRL line 215 which is coupled to the arm processor 210 and each of the nodes 211, 212, 213 of the robotic arm 211. When one of the arm processor 210 and the nodes 211, 212, 213 detects a fault affecting it, the arm processor or node can pull the FRL line 215 HIGH to quickly propagate a fault notification to other components coupled to the line 215. Conversely, when the arm processor 210 is to transmit a recovery notification to the nodes of the robotic arm 111, it may pull the FRL line 215 LOW to quickly propagate the recovery notification to other components coupled to the line 215.

Although a real FRL line 215 is described herein, it is to be appreciated that a virtual FRL line 215 may alternatively be used by designating one or more fields of the packets as including such fault and recovery notifications. For example, the presence of a "1" in a designated bit of the packet may indicate a fault notification and the absence of a "1" (i.e., a "0") in the designated bit (or a different bit) of the packet may indicate a recovery notification. For additional details on such a virtual FRL line, see, e.g., the previously incorporated by reference U.S. Pat. No. 8,054,752 entitled "Synchronous Data Communication."

Figure 3:
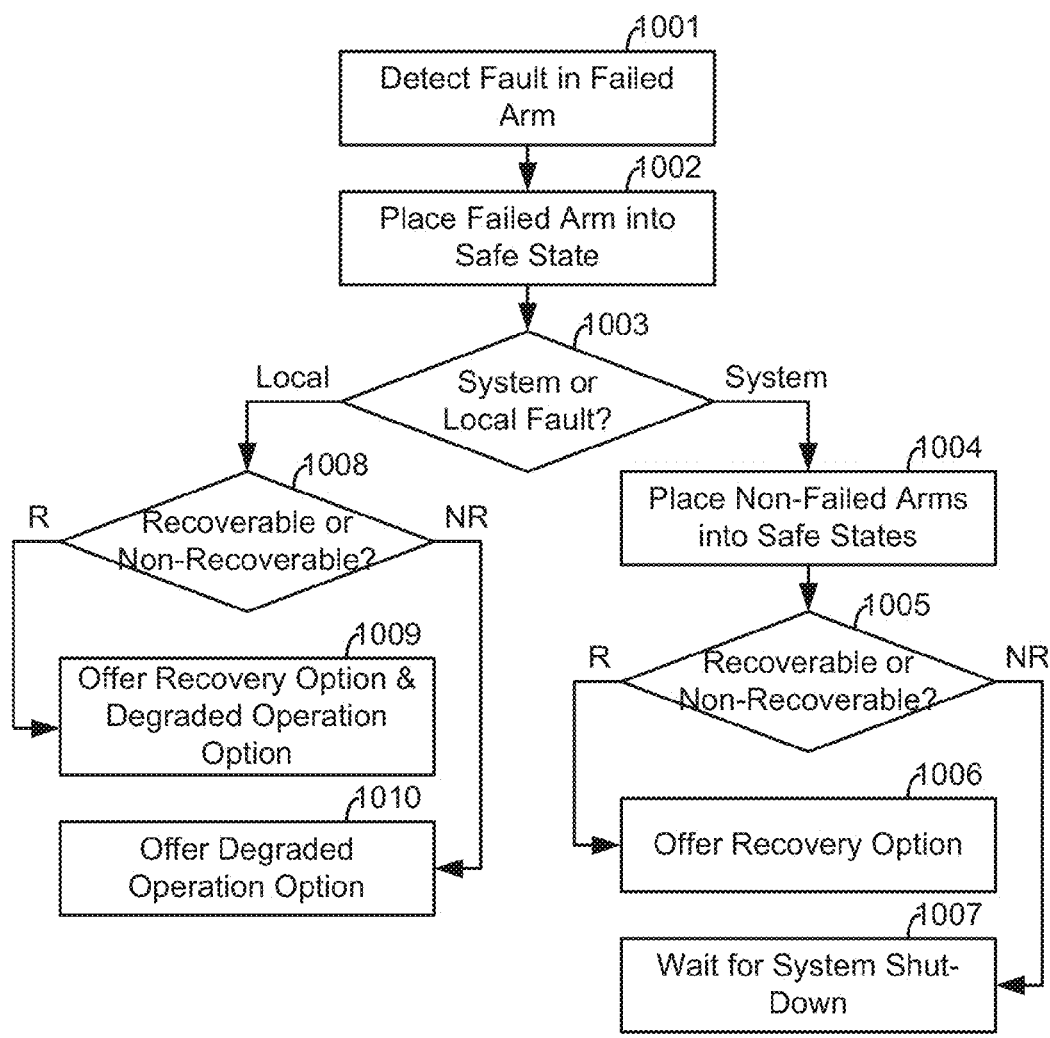
FIG. 3 illustrates a flow diagram of a method for providing fault reaction, fault isolation, and graceful degradation.

FIG. 3 illustrates, as an example, a method for fault reaction, fault isolation, and graceful degradation that may be implemented in a robotic system having a plurality of robotic arms. In block 1001, the method detects a fault in a failed arm of the plurality of robotic arms, wherein the robotic arm becomes a "failed arm" because of the detected fault. In block 1002, the method then places the failed arm into a safe state, wherein a "safe state" refers to a state of the failed arm that isolates the detected fault by preventing further movement of the arm. In block 1003, the method determines whether the fault should be treated as a system fault or a local fault, wherein a "system fault" refers to fault that affects the performance of at least one other robotic arm of the plurality of robotic arms and a "local fault" refers to a fault that affects the performance of only the failed arm. In particular, since a local fault results in only the failed arm being kept in a safe state until the fault is cleared, it should not be the type of fault which would result in unsafe operation of the non-failed robotic arms. Therefore, if the fault is of the type that would result in unsafe operation of the non-failed arms, then the method should result in a determination that the detected fault is a system fault in which all robotic arms in the system are to be placed in a safe state. In block 1004, the method places the non-failed arms of the plurality of arms into safe states only if the fault is to be treated as a system fault, wherein "non-failed arms" refers to robotic arms of the plurality of robotic arms in which no faults have been detected.

The method may also perform various optional tasks. In block 1005, the method optionally determines whether the detected fault is classified as a recoverable system fault or a non-recoverable system fault. In block 1006, the method optionally offers the user of the system a recovery option if the fault is classified as a recoverable system fault. On the other hand, in block 1007, the method optionally waits for system shut-down if the fault is classified as a non-recoverable system fault.

Further, if the determination in block 1003 is the fault is to be treated as a local fault, then in block 1008, the method optionally determines whether the fault is classified as a recoverable local fault or a non-recoverable local fault. In block 1009, the method optionally offers the user of the system a recovery option and a degraded operation option if the fault is classified as a recoverable local fault. On the other hand, in block 1010, the method optionally only offers a degraded operation option if the fault is classified as a non-recoverable local fault.

Additional optional aspects may also be included in the method for fault reaction and graceful degradation of the robotic system in accordance with the cooperative interaction of the nodes of the robotic arms, the arm processors associated with the robotic arms, the arm supervisor processor, and the system supervisor processor as described in the following flow diagrams.

Figure 4:
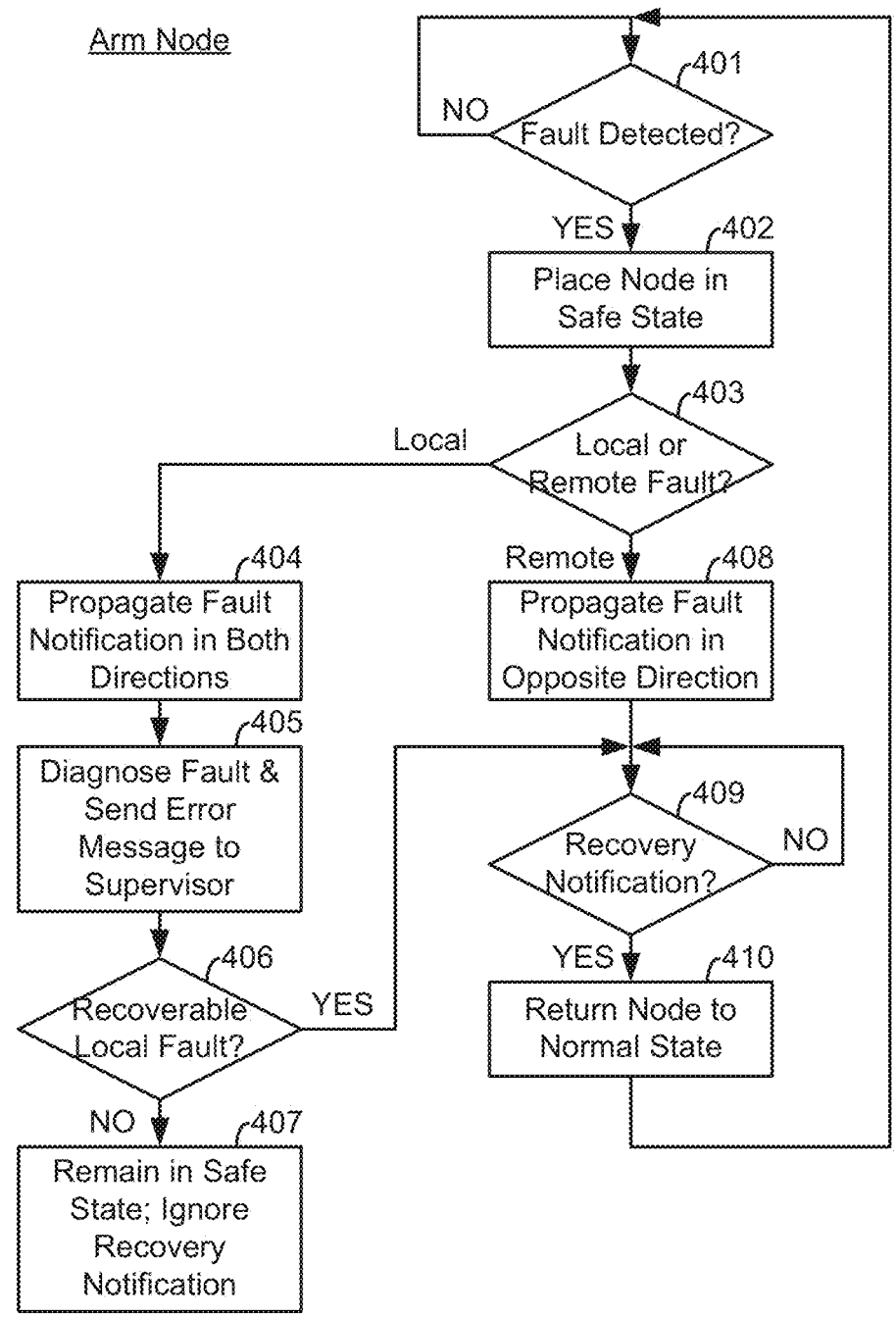
FIG. 4 illustrates a flow diagram of aspects of a method for providing fault reaction, fault isolation, and graceful degradation that are preferably performed by nodes of the robotic arms of the robotic system.

FIG. 4 illustrates, as an example, a flow diagram of aspects of a method for performing fault reaction, fault isolation, and graceful degradation that are preferably performed by each of the nodes (e.g., 211, 212, 213) of the plurality of robotic arms of the robotic system 1000.

In block 401, each node continuously monitors signals and/or information in the node to detect a fault affecting the node using conventional fault detection methods. This type of detected fault is referred to herein as a "local fault", because it is local to the node. The node also monitors the FRL line (real or virtual) for a fault notification issued by its arm processor or another node in its robotic arm. This type of detected fault is referred to herein as a "remote fault", because it is not local to the node. The detected fault may be hardware, firmware, software, environment, or communication related. For descriptive purposes, the node in which a fault has been detected is referred to herein as a "failed node" and as previously explained, its robotic arm is referred to herein as a "failed arm". Nodes in which no fault has been detected are referred to herein as "non-failed nodes" and as previously explained, robotic arms in which no fault has been detected are referred to herein as "non-failed arms".

In block 402, once a fault is detected in block 401, the node places itself in a safe state. This may be done, for example, by disabling the node's one or more controlled motors (e.g., ceasing to provide voltage signals to the one or more motors). Alternatively or additionally, this may be done by engaging the node's one or more controlled brakes (e.g., energizing the node's one or more brakes to inhibit rotations of the node's one or more motors). In block 403, the node determines whether the detected fault is a local fault or a remote fault. As previously explained in reference to block 401, the source of the fault determines whether it is to be treated as a local fault or a remote fault. If the fault is determined to be a local fault, then the node is a failed node. In this first case, the failed node continues by performing blocks 404-407 and blocks 409-410 as described below. On the other hand, if the fault is determined to be a remote fault, then the node is a non-failed node. In this second case, the non-failed node continues by performing blocks 408-410 as described below.

In block 404, the failed node propagates a fault notification to adjacent nodes in both upstream and downstream directions in the failed robotic arm. As used herein, the "downstream" direction refers to packets of information traveling away from the node's arm processor and the "upstream" direction refers to packets of information traveling towards the node's arm processor. As previously explained, one way the node may do this is by pulling the FRL line (actual or virtual) to a HIGH state.

In block 405, the failed node then diagnoses the fault and sends an error message to the system supervisor processor 201. The error message preferably contains information of the fault such as its error code, error class, and origin. Each type of error that may occur affecting the node is assigned an error code. The error codes are classified into error classes. Preferably, there are at least four error classes: recoverable arm faults (also referred to herein as "recoverable local faults"), non-recoverable arm faults (also referred to herein as "non-recoverable local faults"), recoverable system faults, and non-recoverable system faults. The term "recoverable" as used herein means the user may be provided with an option to attempt recovery from the fault. The term "non-recoverable" as used herein means the user may not be provided with the option to attempt recovery from the fault. The origin of the fault includes information of the identity of the node and optionally additional information of the source of the fault in the node.

In block 406, the failed node determines whether or not the detected fault is a recoverable local fault. As previously explained, it makes this determination by the error class of the fault. If the determination in block 406 is NO (e.g., the detected fault is a non-recoverable local fault), then in block 407, the failed node remains in its safe state and ignores any recovery notification that it may subsequently receive on the FRL line (actual or virtual). On the other hand, if the determination in block 406 is YES (e.g., the detected fault is a recoverable local fault), then the failed node proceeds to block 409.

If the determination in block 403 is that the detected fault is to be treated as a remote fault (i.e., the node is a non-failed node), then in block 408, the non-failed node propagates the received fault notification in the opposite direction from whence it came if a virtual FRL line is employed (e.g., if the fault notification is received by node 212 from node 211, then node 212 propagates the fault notification to node 213). In the case of a real FRL line, the non-failed node needs to take no action for such propagation of the fault notification.

In block 409, both the failed node and non-failed node wait for a recovery notification to be received. In block 410, once a recovery notification is received, the node returns itself from the safe state back to its normal operating state. Typically, this may be done by reversing actions taken in block 402 while avoiding abrupt changes. The node then goes back to performing its fault detection tasks described in reference to block 401.

Figure 5:
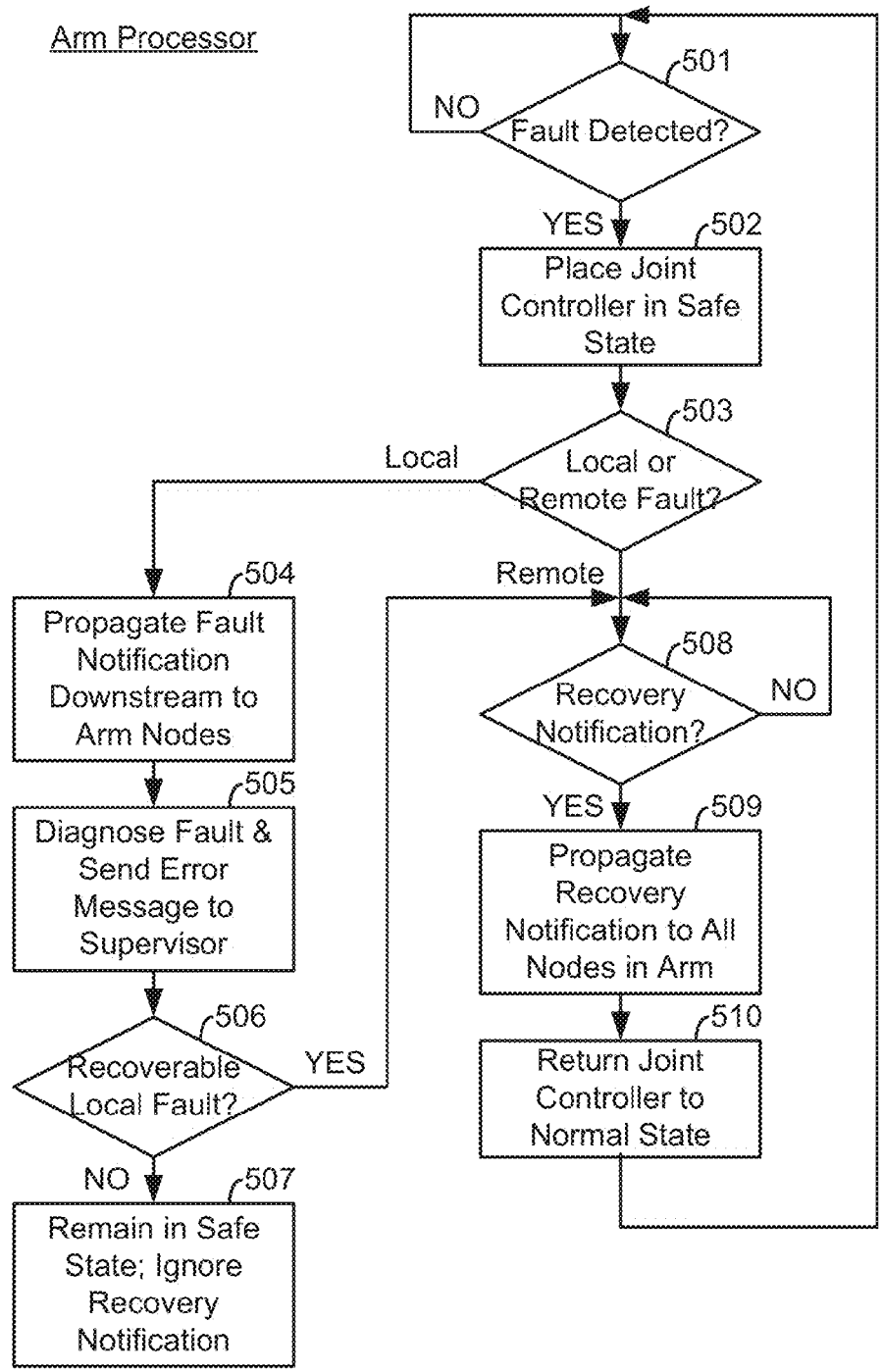
FIG. 5 illustrates a flow diagram of aspects of a method for providing fault reaction, fault isolation, and graceful degradation that are preferably performed by arm processors that are operatively coupled to the robotic arms of the robotic system.

FIG. 5 illustrates, as an example, a flow diagram of aspects of a method for performing fault reaction, fault isolation, and graceful degradation that are preferably performed by each arm processor (e.g., 210, 220, 230, 240) that is operatively coupled to a robotic arm of the robotic system 1000.

In block 501, each arm processor, while performing its normal operating tasks, also continuously monitors its own operation and looks out for a fault notification propagated by a failed node in its operatively coupled robotic arm. If a fault is detected while monitoring its own operation, then the fault is referred to herein as being a "local fault". On the other hand, if the fault is detected by receiving a fault notification from a failed node in its operatively coupled robotic arm, then the fault is referred to herein as being a "remote fault". A remote fault in this case refers to a fault notification propagated along the FRL line (real or virtual) by a failed node in the robotic arm to which the arm processor is operatively coupled to.

If a fault has been detected in block 501, then in block 502, the arm processor places its joint position controller in a safe state by latching its output motor current commands $\hat{I}_C$ to zero. This serves to reinforce the safe states of their respective nodes.

In block 503, the arm processor determines whether the detected fault is a local fault or a remote fault. As previously explained in reference to block 501, the source of the fault determines whether it is to be treated as a local fault or a remote fault. If the fault is determined to be a local fault, then the arm processor is treated as a failed node. In this first case, the arm processor continues by performing blocks 504-507 and blocks 509-510 as described below. On the other hand, if the fault is determined to be a remote fault, then the arm processor is treated as a non-failed node. In this second case, the arm processor continues by performing blocks 508-510 as described below.

In block 504, the arm processor propagates a fault notification downstream to all nodes of its operatively connected robotic arm. As previously explained, one way the arm processor may do this is by pulling the FRL line (actual or virtual) to a HIGH state.

In block 505, the arm processor then diagnoses the fault and sends an error message to the system supervisor processor 201. The error message preferably contains information of the fault such as its error code, error class, and origin. Each type of error that may occur affecting the arm processor is assigned an error code. The error codes are classified into error classes. Preferably, there are at least four error classes: recoverable processor faults, non-recoverable processor faults, recoverable system faults, and non-recoverable system faults. The terms "recoverable" and "non-recoverable" are used herein in a similar manner as described in reference to block 405 of FIG. 4. The origin of the fault includes information of the identity of the arm processor and optionally additional information of the source of the fault in the arm processor.

In block 506, the arm processor determines whether or not the detected fault is a recoverable local fault. As previously explained, it makes this determination by the error class of the fault. If the determination in block 506 is NO (e.g., the detected fault is a non-recoverable local fault), then in block 507, the joint position controller of the failed arm processor remains in its safe state and the arm processor ignores any recovery notification that it may subsequently receive on the FRL line (actual or virtual). On the other hand, if the determination in block 506 is YES (e.g., the detected fault is a recoverable local fault), then the arm processor proceeds to block 508.

If the determination in block 503 is that the detected fault is to be treated as a remote fault, then in block 508, the arm processor waits for a recovery notification to be received from the system supervisor processor 201. In block 509, once a recovery notification is received, the arm processor propagates the recovery notification to all nodes in its operatively coupled robotic arm by, for example, pulling its FRL line (real or virtual) to LOW. In block 510, the arm processor then returns its joint position controller from the safe state back to its normal operating state. Typically, this may be done by releasing its output motor current commands $\hat{I}_C$ so that they once again reflect the desired joint positions $\hat{\theta}_C$ of its operatively coupled robotic arm, while avoiding abrupt changes. The arm processor then goes back to performing its fault detection tasks described in reference to block 501.

Figure 6:
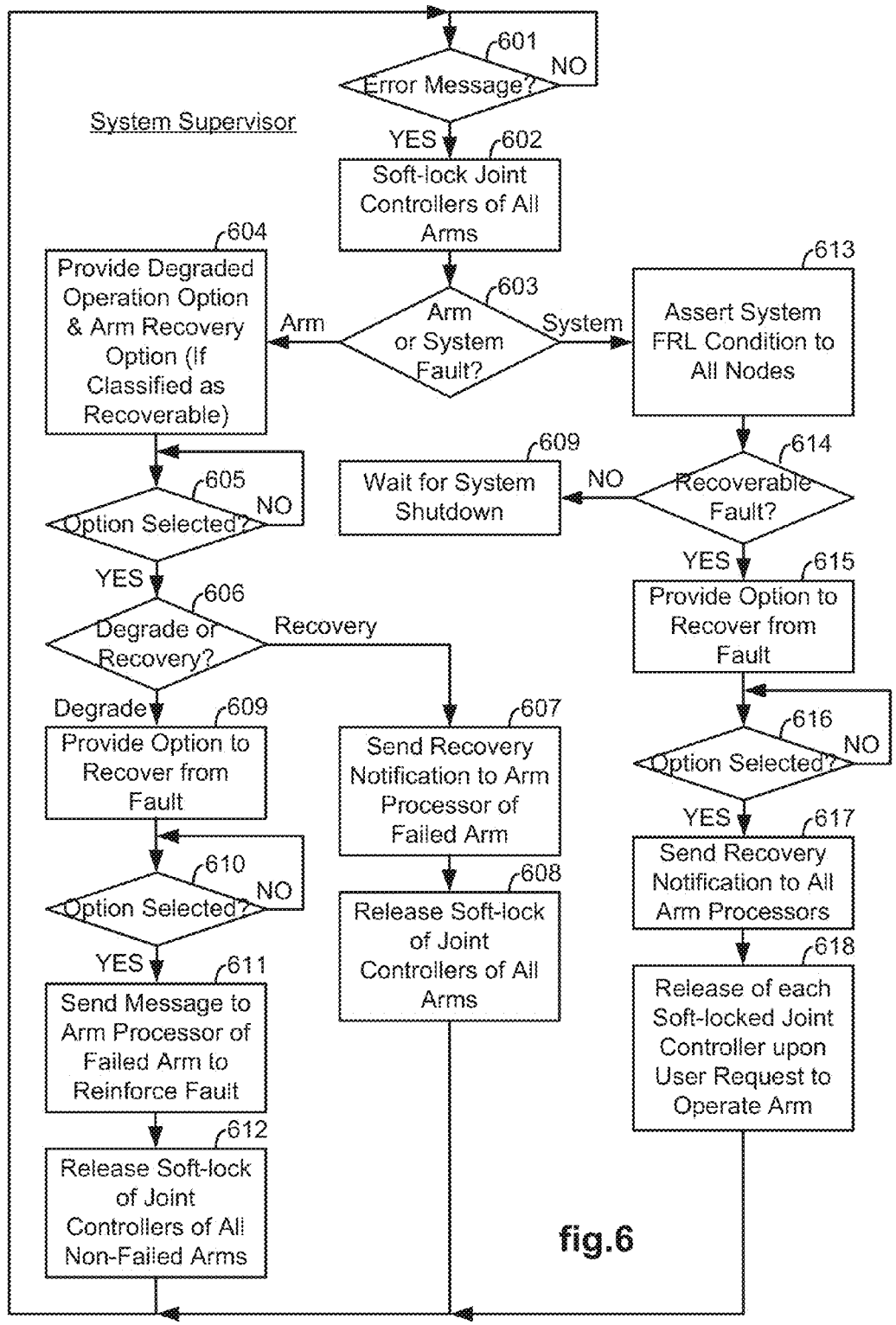
FIG. 6 illustrates a flow diagram of aspects of a method for providing fault reaction, fault isolation, and graceful degradation that are preferably performed by a system supervisor processor of the robotic system.

FIG. 6 illustrates, as an example, a flow diagram of aspects of a method for performing fault reaction, fault isolation, and graceful degradation that are preferably performed by the system supervisor processor 201 of the robotic system 1000.

In block 601, the system supervisor processor, while performing its normal operating tasks, also waits to receive an error message transmitted from another component of the robotic system 1000. For example, such an error message may have been transmitted by a failed node as described in reference to block 405 of FIG. 4 or it may have been transmitted by a failed arm processor as described in reference to block 505 of FIG. 5.

Once an error message is received in block 601, in block 602, the system supervisor processor halts the system for safety purposes by, for example, commanding joint position controllers of all arm processors (e.g., 210, 220, 230, 240) in the robotic system to latch their respective outputs at their current values. In this way, no new current command inputs are provided to the robotic arms until the outputs of the joint position controllers are unlatched. This latching of the outputs of the joint position controllers is referred to herein as "soft-locking" the joint position controllers. The method then proceeds to block 603.

In block 603, the system supervisor processor determines whether the detected fault should be treated as a system fault or an arm fault. Preferably, the system supervisor processor does this by inspecting the error class information provided in the error message. In this case, a system fault includes all faults classified as either a recoverable or non-recoverable system fault, since these faults are applicable to more than the failed robotic arm. Conversely, an arm fault includes all faults classified as either a recoverable or non-recoverable local fault, since these faults are applicable only to the failed robotic arm.

Blocks 604-612 are performed for all faults that are to be treated as arm faults. In block 604, the system supervisor processor provides the user of the robotic system 1000 with an option to accept degraded operation of the robotic system 1000. Further, if the local fault is a recoverable local fault, the system supervisor processor also provides the user with an option to recover from the fault. Preferably, in addition to each provided option, information of the detected fault may also be provided by the system supervisor processor to assist the user in deciding whether or not to accept the option. Preferably, the options and fault information are provided on a display screen which is viewable by the user, such as the stereo viewer 101 of the user console 100. However, any conventional means for providing such options and information to the user is also contemplated as being usable by the system supervisor processor in performing its tasks herein.

In block 605, the system supervisor processor waits for the user to select an option provided in block 604. Once an option is selected by the user, in block 606, the system supervisor processor determines whether the selected option was the degraded operation option or the recovery option.

If a recovery option was provided and the user selects the recovery option, then in block 607, the system supervisor processor sends a recovery notification to the arm processor of the failed robotic arm. The arm processor of the failed robotic arm would then process the recovery notification as previously described in reference to blocks 508-510 of FIG. 5, which includes propagating the recovery notification to all nodes of the failed arm. The nodes of the failed arm would then process the recovery notification as previously described in reference to blocks 409-410 of FIG. 4. In block 608, the system supervisor processor then releases the soft-lock of the joint controllers of all arm processors by unlatching their outputs so that they may once again issue motor current commands $\hat{I}_C$ which reflect the desired joint positions $\hat{\theta}_C$ of their operatively coupled robotic arms. The system supervisor processor then goes back to performing its tasks described in reference to block 601.

Note that after attempting to recover a fault as described above in reference to blocks 607-608, if the fault is a persistent fault (i.e., one that does not go away), then the origin of the fault will once again trigger a detected fault in either block 401 of FIG. 4 or block 501 of FIG. 5. In this case, presumably the user of the system will choose not to select the recovery option in a subsequent pass through blocks 604-605 if repeated attempts to recover from the fault result in repeated failures.

If the user selects the degraded operation option, however, then in block 609, the system supervisor processor provides the user with an option to recover from the fault. Recovery from the fault in this case differs from the recovery described in reference to blocks 607-608 in that no attempt is made to recover the failed arm. Recovery only applies to recovering normal operation of the non-failed arms. In block 610, the system supervisor processor waits for the user to select the option provided in block 609. Once the option is selected by the user, in block 611, the system supervisor processor sends a message to the arm processor of the failed arm to reinforce the fault. Reinforcement of the fault in this case means additional steps are taken to fully shut-down operation of the failed robotic arm. One example of such a reinforcement measure is to operatively disconnect the joint position controller of the arm processor from other parts of a master/slave control system which generates the desired joint positions $\hat{\theta}_C$ of its operatively coupled robotic arm. Another reinforcement measure may be to turn off power to the failed robotic arm. In block 612, the system supervisor processor then releases the soft-lock of the joint controllers of the arm processors of all non-failed arms by unlatching their outputs so that they may once again issue motor current commands $\hat{I}_C$ which reflect the desired joint positions $\hat{\theta}_C$ of their operatively coupled robotic arms. The system supervisor processor then goes back to performing its tasks described in reference to block 601.

Blocks 613-618 are performed for all faults that are to be treated as system faults. In block 613, the system supervisor processor asserts a system FRL condition to all nodes in the robotic system 1000. Preferably, it does this by causing the FRL lines 215, 225, 235, 245 (which may be actual or virtual lines) to be pulled HIGH so that fault notifications are simultaneously provided to the arm processors and nodes of the robotic arms 111, 113, 115, 117.

In block 614, the system supervisor processor then determines whether or not the system fault is a recoverable system fault. As previously explained, it may do this by inspection of the error class in the received error message. If the determination in block 614 is NO (i.e., the system fault is a non-recoverable system fault), then in block 609, the system supervisor processor takes no further action and waits for the system to be shut-down.

On the other hand, if the determination in block 614 is YES (i.e., the system fault is a recoverable system fault), then in block 615, the system supervisor processor provides the user with an option to recover from the fault. In block 616, the supervisor processor waits for the user to select the recovery option. Once the option is selected by the user, in block 617, the system supervisor processor sends a recovery notification to the arm processors of all robotic arms of the robotic system 1000. The arm processors would then process the recovery notification as previously described in reference to blocks 508-510 of FIG. 5, which includes propagating the recovery notification to all nodes of their respective arms. The nodes would then process the recovery notification as previously described in reference to blocks 409-410 of FIG. 4. In block 618, the system supervisor processor releases the soft-lock of each joint controller upon receiving a request or action from the user to operate the joint controller's arm in its normal operating state so that the released joint controller may once again issue motor current commands $\hat{\mathrm{I}}_C$ which reflect the desired joint positions $\hat{\theta}_C$ of its operatively coupled robotic arm. The system supervisor processor then goes back to performing its tasks described in reference to block 601.

Note that after attempting to recover a fault as described above in reference to blocks 614-618, if the fault is a persistent fault (i.e., one that does not go away), then the origin of the fault will once again trigger a detected fault in either block 401 of FIG. 4 or block 501 of FIG. 5. In this case, presumably the user of the system will choose not to select the recovery option in a subsequent pass through blocks 615-616 if repeated attempts to recover from the fault result in repeated failures.

Figure 7:
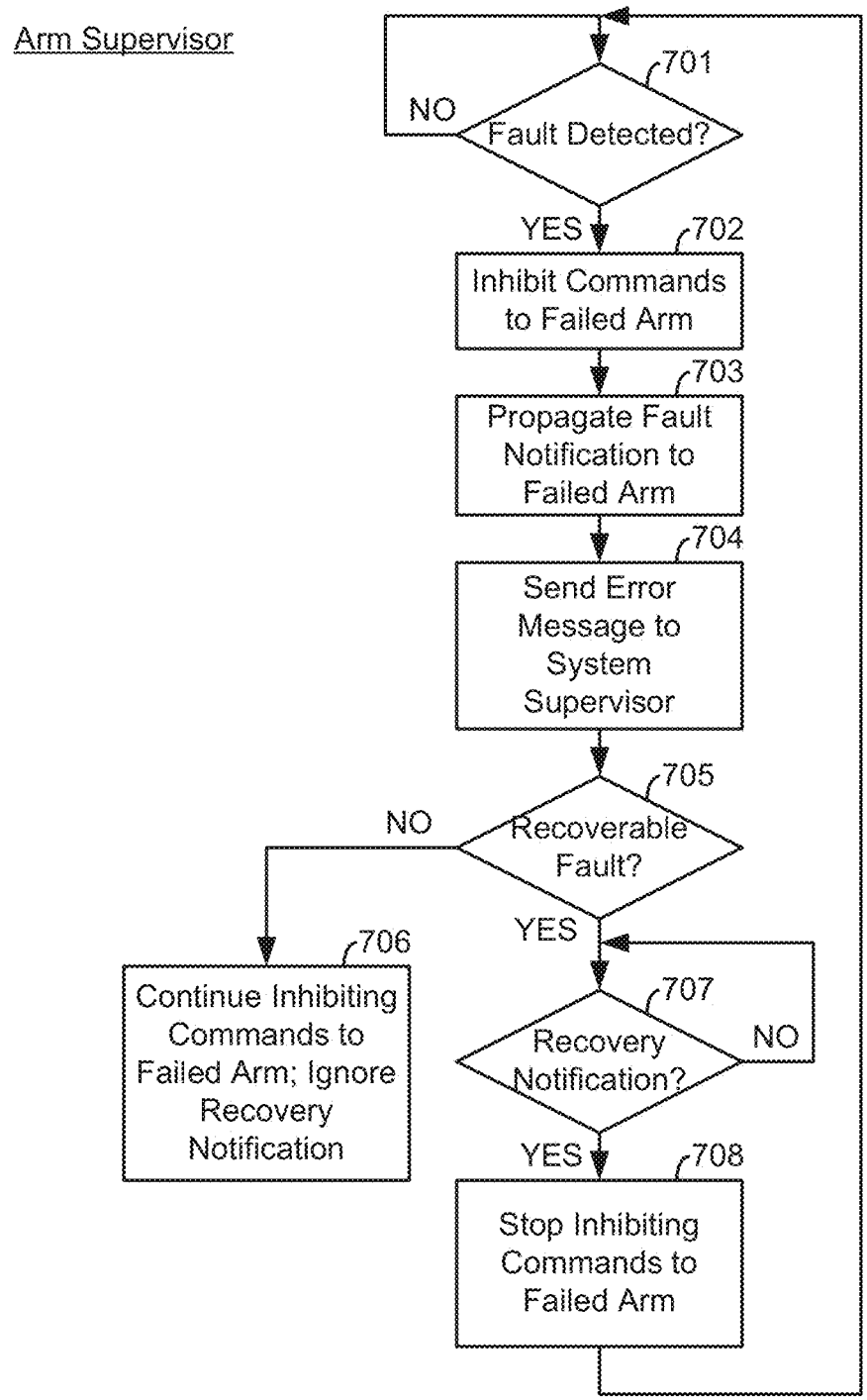
FIG. 7 illustrates a flow diagram of aspects of a method for providing fault reaction, fault isolation, and graceful degradation that are preferably performed by an arm supervisor processor of the robotic system.

FIG. 7 illustrates, as an example, a flow diagram of aspects of a method for performing fault reaction, fault isolation, and graceful degradation that are preferably performed by an arm supervisor processor (e.g., 250) that is operatively coupled to a system supervisor processor (e.g., 201) and arm processors (e.g., 210, 220, 230, 240) of the robotic system 1000.

As previously described, the arm supervisor processor 250 may initiate, control, and/or monitor certain coordinated activities of the arms 111, 113, 115, 117 of the robotic system 1000. As an example, the arm supervisor 250 may initiate and monitor a start-up brake test wherein the arm supervisor 250 communicates with each of the arm processors 210, 220, 230, so that a specific brake sequence with different torque values is applied to the brakes of their respective robotic arms. The coordination of this activity is done in this case by the arm supervisor 250 since the overhead to code this into each arm processor may be excessive. At the end of each sequence, a maximum Torque value computed by each arm processor is passed back to the arm supervisor 250 and if an out of range error occurs, the arm supervisor 250 will post a fault notification to the failed arm. So in this example, the arm supervisor commands the arm processors to perform the arm activity, monitors the results, and decides if the activity results indicate an arm failure.

In block 701, the arm supervisor monitors the coordinated activity of the robotic arms, as reported by their respective arm processors, to detect a fault in one of the arms. Typically, the arm supervisor determines a fault has occurred when a reported measurement exceeds an expected value by a threshold amount. The fault being detected in this case is a fault that would not ordinarily be detected by one of the nodes or the arm processor of the robotic arms.

After a fault has been detected in block 701, then in block 702, the arm supervisor inhibits any further commands to the failed arm. In particular, no further commands will be transmitted from the arm supervisor to the arm processor of the failed arm until either a recovery notification is received from the system supervisor or the system is restarted.

In block 703, the arm supervisor propagates a fault notification to the failed arm by pulling the FRL line of the failed arm to a HIGH state. In the case of a virtual FRL line, the arm supervisor may transmit the fault notification in the same or a different packet field than that designated for transmission of a fault notification by one of the nodes or the arm processor of the failed arm.

In block 704, the arm supervisor sends an error message to the system supervisor with available details of the fault such as an error code, error class, and origin. Each type of fault that may be detected by the arm supervisor is assigned an error code and the error codes are classified into error classes such as recoverable arm faults, non-recoverable arm faults, recoverable system faults, and non-recoverable system faults. The origin of the fault includes information of the identity of the failed arm and optionally additional information of the source of the fault if available. The system supervisor then proceeds to process the error message as described in reference to block 601 of FIG. 6.

In block 705, the arm supervisor determines whether or not the detected fault is a recoverable fault. As previously explained, it makes this determination according to the error class of the fault. If the determination in block 705 is NO (e.g., the detected fault is a non-recoverable arm or system fault), then in block 706, the arm supervisor continues to inhibit any further commands to the failed arm and ignores any recovery notification that it may subsequently receive from the system supervisor, On the other hand, if the determination in block 705 is YES (e.g., the detected fault is a recoverable arm or system fault), then in block 707, the arm supervisor waits for a recovery notification to be received from the supervisor processor. In block 708, once a recovery notification is received, the arm supervisor stops inhibiting commands to the failed arm and goes back to its normal operating mode and performing its fault detection tasks described in reference to block 701.

Although the various aspects of the present invention have been described with respect to the above examples, it will be understood that the invention is entitled to full protection within the full scope of the appended claims. In particular, although certain specific examples are described herein, the scope of the invention is not to be limited to these specific examples. For example, fault isolation and graceful degradation may be extended down to the failed node level so that the user may be provided an option to continue using non-failed nodes of a failed arm. As another example, non-failed nodes or the arm processor of a failed arm may be adapted to detect faults in a failed node of the failed arm, propagate a fault notification to other nodes of the failed arm, and send an error message to the system supervisor processor. Still other examples readily envisioned and implemented by a person of ordinary skill in the robotic arts which extend the teachings described herein are also contemplated to be within the full scope of the present invention.

We claim:

1. A method for fault reaction, fault isolation, and graceful degradation in a robotic system having a plurality of robotic arms, the method comprising:
   detecting a fault in a failed arm of the plurality of robotic arms;
   placing the failed arm into a safe state;
   determining whether the fault should be treated as a system fault or a local fault; and
   placing non-failed arms of the plurality of robotic arms in the safe state only if the fault is to be treated as a system fault.

2. The method of claim 1, further comprising:
   providing a degraded operation option to a user of the robotic system if the fault is determined to be a local fault; and
   providing a recovery option to the user if the fault is determined to be a recoverable local fault or a recoverable system fault.

3. The method of claim 1, wherein each of the plurality of robotic arms has a plurality of motors for actuating corresponding degrees of freedom of the robotic arm, and wherein placing the failed arm into a safe state comprises:
   disabling the plurality of motors for the failed arm.

4. The method of claim 1, wherein each of the plurality of robotic arms has a plurality of brakes for halting movement in corresponding degrees of freedom of the robotic arm, and wherein placing the failed arm into a safe state comprises: engaging the plurality of brakes for the failed arm.

5. The method of claim 1, wherein each of the plurality of robotic arms has one or more nodes for controlling one or more motors which effect corresponding degrees of freedom movement of the robotic arm, wherein the detecting a fault in a failed arm of the plurality of robotic arms comprises detecting the fault in one of the nodes of the failed arm, and wherein the placing the failed arm into a safe state includes placing each node of the failed arm in the safe state.

6. The method of claim 1, wherein each of the plurality of robotic arms has an arm processor operatively coupled to the robotic arm, wherein the detecting a fault in a failed arm of the plurality of robotic arms comprises detecting the fault in one of the arm processors, and wherein the placing the failed arm into a safe state includes placing the arm processor in the safe state.

7. The method of claim 1, wherein the detecting a fault in a failed arm of the plurality of robotic arms comprises monitoring coordinated activities of the plurality of robotic arms, and wherein the placing the failed arm into a safe state includes inhibiting commands to the failed arm.

8. The method of claim 1, wherein the determining whether the fault should be treated as a system fault or a local fault comprises:
diagnosing the fault; and
determining the fault is to be treated as a system fault if the diagnosis of the fault indicates that it would be unsafe to operate the non-failed arms.

9. A robotic system comprising:
a plurality of robotic arms;
a plurality of arm processors, wherein each of the plurality of arm processors is operatively coupled to a corresponding one of the plurality of robotic arms; and
a system supervisor processor;
wherein each robotic arm has a plurality of motors for actuating degrees of freedom movement of the robotic arm; wherein each robotic arm has one or more nodes for controlling corresponding motors of the robotic arm; wherein each node and arm processor is configured to detect an occurrence of a fault affecting the node or arm processor, to place the node or arm processor into a safe state upon detecting the occurrence of the fault, to propagate a fault notification through a failed arm that includes the node or is operatively coupled to the arm processor, to diagnose the fault, and to send an error message including information of the fault to the system supervisor processor; and wherein each node of the plurality of robotic arms and each arm processor operatively coupled to the plurality of robotic arms is configured to place the node or arm processor into a safe state upon receiving a fault notification from another source; and
wherein the system supervisor processor is configured to receive the error message from the failed node or the arm processor, to determine whether the detected fault is to be treated as a system fault or a local fault by using information in the error message, and to transmit a fault notification to the arm processors of non-failed arms of plurality of robotic arms only if the detected fault is to be treated as a system fault.

10. The robotic system of claim 9, wherein the system supervisor processor is configured to provide a degraded operation option to a user of the robotic system if the fault is determined to be a local fault, and provide a recovery option to the user if the fault is determined to be a recoverable local fault or a recoverable system fault.

11. The robotic system of claim 10, wherein the system supervisor processor is configured to send a message to the arm processor operatively coupled to the failed arm to reinforce the fault by fully shutting-down operation of the failed arm if the degraded operation option is selected.

12. The robotic system of claim 10, wherein the system supervisor processor is configured to send a recovery notification to the arm processor of the failed arm if the recovery option is selected and the fault is determined to be the local fault.

13. The robotic system of claim 10, wherein the system supervisor processor is configured to send a recovery notification to each arm processor of the plurality of robotic arms if the recovery option is selected and the fault is determined to be the system fault.

14. The robotic system of claim 9, wherein each node places the node into a safe state by at least disabling the one or more motors controlled by the node.

15. The robotic system of claim 9, wherein each of the plurality of robotic arms has a plurality of brakes for halting movement of corresponding motors of the robotic arm, and wherein each node places the node into a safe state by at least engaging one or more brakes controlled by the node.

16. The robotic system of claim 9, wherein the plurality of nodes and the arm processor of the failed arm are configured to place the failed arm into the safe state by placing each node of the plurality of nodes and the arm processor of the failed arm in the safe state.

17. The robotic system of claim 9, wherein each arm processor includes a joint position controller that the arm processor places into a safe state by latching an output of the joint position controller to a zero value upon detecting a fault in the arm processor or receiving a fault notification from another source.

18. The robotic system of claim 9, further comprising:
an arm supervisor processor operatively coupled to the system supervisor processor and the plurality of arm processors, wherein the arm supervisor processor is configured to monitor coordinated activities of the plurality of robotic arms to detect an occurrence of a fault affecting a failed arm of the plurality of robotic arms during the coordinated activities, to inhibit commands and propagate a fault notification to the failed arm, and to send an error message including information of the fault to the system supervisor processor for processing by the system supervisor processor.

* * * * *